United States Patent
Cimino et al.

(10) Patent No.: US 6,716,194 B1
(45) Date of Patent: Apr. 6, 2004

(54) SURGICAL ASPIRATION DEVICE EMPLOYING CONTINUOUS, PRECISE VENTING

(75) Inventors: William W. Cimino, Louisville, CO (US); Peter D. Geary, Erie, CO (US)

(73) Assignee: Sound Surgical Technologies LLC, Louisville, CO (US)

( * ) Notice: Subject to any disclaimer, the term of this patent is extended or adjusted under 35 U.S.C. 154(b) by 0 days.

(21) Appl. No.: 10/138,403

(22) Filed: May 3, 2002

Related U.S. Application Data

(60) Provisional application No. 60/289,032, filed on May 4, 2001.

(51) Int. Cl.⁷ .................................................. A61M 1/00
(52) U.S. Cl. ...................................................... 604/119
(58) Field of Search ................. 604/119, 902, 604/118, 246, 249, 30, 33, 313, 315, 316

(56) References Cited

U.S. PATENT DOCUMENTS

| | | | |
|---|---|---|---|
| 4,079,965 A | * 3/1978 | Moughty et al. | 285/7 |
| 4,468,217 A | * 8/1984 | Kuzmick et al. | 604/48 |
| 4,536,180 A | 8/1985 | Johnson | 604/268 |
| 4,568,332 A | * 2/1986 | Shippert | 604/119 |
| 4,596,553 A | 6/1986 | Lee | 604/542 |
| 4,735,605 A | 4/1988 | Schwartz | 604/22 |
| 5,013,300 A | 5/1991 | Williams | 604/119 |
| 5,112,302 A | 5/1992 | Cucin | 604/35 |
| 5,181,907 A | 1/1993 | Becker | 604/22 |
| 5,320,328 A | * 6/1994 | Decloux et al. | 251/326 |
| 5,348,535 A | 9/1994 | Cucin | 604/35 |
| 5,569,178 A | 10/1996 | Henley | 604/22 |
| 5,643,198 A | 7/1997 | Cucin | 604/22 |
| 5,665,101 A | 9/1997 | Becker | 606/180 |
| 5,899,884 A | * 5/1999 | Cover et al. | 604/119 |
| 6,129,701 A | * 10/2000 | Cimino | 604/35 |

\* cited by examiner

*Primary Examiner*—Sharon Kennedy
(74) *Attorney, Agent, or Firm*—Merchant & Gould P.C.

(57) ABSTRACT

The invention relates to an improved surgical instrument and method for the aspiration of tissues and fluids from a patient via suction through a small diameter cannula. The device and method achieve improved results (e.g., speed and efficiency of the surgical procedure) using a continuous, precise amount of vented air of between about 3 and about 40 cubic feet per hour.

15 Claims, 2 Drawing Sheets

SURGICAL ASPIRATION DEVICE EMPLOYING CONTINUOUS, PRECISE VENTING

This application claims the benefit of Provisional application Ser. No. 60/289,032, filed May 4, 2001.

I. BACKGROUND OF THE INVENTION

This invention relates generally to surgical instruments, and, more particularly, to a surgical device for use in aspirating tissue and fluids from a patient.

Liposuction is a surgical procedure for altering the human form, specifically by removal of localized deposits of fat tissues that are unresponsive to diet or exercise. The procedure is also known as suction lipectomy, lipolysis, and more recently as body contour surgery or body sculpting surgery. It is most often performed by plastic surgeons, although dermatologists, gynecologists, and other surgical specialties also perform the procedure.

The procedure is typically accomplished by inserting a small diameter hollow cannula through an incision in the skin, applying a suction source to the end of the cannula that remains outside of the body, and forcing the working end of the cannula forward and backward in the layer of fatty tissue. The fatty tissue is torn, crushed, or avulsed, and is then aspirated through small openings along the sides of the hollow cannula near the tip and then through a length of suction tubing to a tissue canister placed in-line with the cannula and the suction source. The procedure may involve multiple incisions and many passes of the cannula in each incision to achieve the desired cosmetic effect for the patient.

A liposuction cannula is typically a small metal tube with a blunt, closed end at the tip. The blunt, closed end at the tip is intended to minimize damage to tissues as the device is thrust forward. Small openings along the sides of the cannula near the tip create passages between the tissue and the central lumen of the cannula, which is in fluid communication with a suction source, so that tissue and fluids can be aspirated. The suction causes the adipose tissue to be pulled into the openings along the sides of the cannula, and the blunt dissection provided by the surgeon's manipulation of the cannula tears the tissue. The fragments and released fluids are then aspirated through the openings along the sides of the cannula and then through the central lumen of the cannula. The liposuction procedure is referred to as a 'closed' procedure because the operative site about the tip of the cannula is not directly visualized during the procedure due to the small incision size and the length of the liposuction cannula, which results in the tip area's being buried inside the tissue.

When a cannula is placed into the fatty tissue through the small incision, a seal is created between the outer surface of the cannula about and along its length and the fatty tissue, preventing the flow of any ambient pressure fluid, such as air, to the operative site about the tip of the cannula. When suction is applied, there exists a level of vacuum inside the cannula at the operative site (the blunt tip area and the side openings) that pulls the tissue into the side openings, which is then torn with the motion of the cannula. Because the seal prevents the flow of any ambient pressure fluid or air to the operative site about the tip or the cannula, the pressure about the tip of the cannula quickly drops to the level of the vacuum of the suction source. The combination of the above-mentioned seal and the fact that the pressure at the operative site about the tip of the cannula has dropped to the level of vacuum of the suction source greatly reduces, if not completely eliminates, the surgeon's ability to remove tissue fragments and fluids from the operative site because the pressure differential between the operative site at the tip of the cannula and the suction source has been eliminated. Thus, tissue fragments and fluids move not at all or very slowly through the cannula and suction tubing. The tip of the cannula must be withdrawn from the patient to such an extent that the seal is broken and the tip and side openings are exposed to ambient air pressure to clear the cannula and suction line. This clearing process removes the tissues and fluids from the cannula and suction tubing and deposits them into the suction canister. At the same time the vacuum level in the suction canister, suction tubing, and cannula is significantly reduced because of the open connection to ambient air. When the cannula is re-inserted into the patient the suction pump begins to pull the air from the canister, suction tubing, and cannula until a good working vacuum is re-established and the system is again functional for aspirating tissue and fluids.

When tissue and fluids are present in the suction tubing they tend to group together and move through the tubing in 'segments'. The segments most often completely fill the inner diameter of the suction tubing for some length and may be separated from each other by air bubbles. Any number of typical segments may be present in the suction tubing at any one time. This fact means that the suction pump and the cannula are not directly connected through a continuous air channel that can be evacuated by the suction pump, rather an 'effective' vacuum is applied to the cannula through the segments and the trapped air bubbles in the suction tubing. This fundamentally limits the vacuum available at the cannula because the trapped air bubbles act as 'gas springs' and expand under the action of the vacuum. The resistance to the movement of the viscous material, both tissue and fluids, in the suction line further reduces the effective vacuum available at the cannula. A long segment of tissue and fluid may have sufficient resistance to movement that the effective vacuum is nil and the cannula must be withdrawn from the patient and the tip exposed to ambient air in order for the segment to pass to the canister. The optimal situation is when the suction tubing is completely clear all the way from the canister to the cannula and a good working vacuum is present. This condition is only achievable for a short period of time with present cannula designs. As soon as viscous tissue and fluids enter the suction line the optimal situation is compromised.

Many patents disclose improvements and solutions for liposuction cannulae. U.S. Pat. No. 4,596,553 to Lee discloses a suction cannula with a guide bar attached to the cannula that is used to control the depth of the cannula in the tissue relative to the skin. U.S. Pat. No. 4,735,605 to Schwartz discloses a suction cannula with an outer tube with a longitudinal slot, and an inner tube with a spiral slot that is movable relative to the outer tube. U.S. Pat. No. 5,112,302 to Cucin has a suction cannula with a reciprocating means so that the cannula can be caused to reciprocate relative to the handle. U.S. Pat. Nos. 5,348,535 and 5,643,198, also to Cucin, have a suction cannula with a hollow outer cannula and a hollow inner cannula connected to a reciprocating means. The hollow inner cannula reciprocates within the hollow outer cannula so that tissue pulled into openings in the hollow outer cannula is sheared between the two cannulae. U.S. Pat. No. 5,181,907 to Becker has a tubular member with a plurality of longitudinally extending members projecting radially outward beyond the surface of the tubular member. U.S. Pat. No. 5,665,101 also to Becker has a method of cutting tissue with a rotary powered surgical instrument with an inner and an outer tube, both with cutting windows on the sides of the tubes. U.S. Pat. No. 5,569,178 to Henley has a source of rotary power, an outer tubing, and an inner tubing with flanges.

U.S. Pat. No. 5,013,300 to Williams has a single lumen cannula, a handle, a means to swivel the handle relative to the cannula, and a plurality of openings in the handle for controlling the suction forces applied to the cannula. The plurality of openings have an aggregate flow area approximately that of the flow area of the bore through the handle. The surgeon uses his or her thumb to uncover the openings to allow a relatively unrestricted flow of ambient air to clear the suction tube. At the same time this process eliminates the vacuum in the cannula. The surgeon then covers the openings to re-establish a vacuum in the cannula, a process that may take tens of seconds depending on the suction pump capability.

U.S. Pat. No. 4,536,180 to Johnson has a suction tube and a valve connected to a second tube passageway that extends within or along the suction tube. The surgeon opens or closes the valve opening in the second tube passageway to provide a source of air to the tip of the suction tube to aid in clearing the cannula and suction tubing.

While some of the patented devices have claimed improvements and solutions to liposuction cannulae for the problems of tissue trauma, surgeon fatigue, cosmetic results, and the frequent need to clear obstructions in the suction line, none addresses or appreciates the above-mentioned problem related to the presence of fluids and tissues in the form of segments with air bubbles in the suction tubing and its direct impact on the effective vacuum available at the cannula. Further, none addresses or appreciates the problem of viscous tissue and fluids moving in the suction tubing and the resulting decrease in effective vacuum at the cannula.

There is a need to improve the design of the prior liposuction cannulae to further increase the efficiency and speed of the tissue and fluid aspiration process. Accordingly, it is the object of the present invention to produce an improved surgical instrument for removal of tissues and fluids from a patient by increasing the effective suction available in the cannula.

II. SUMMARY OF THE INVENTION

An improved cannula for liposuction is provided using a continuous, precision "leak" in the handle or cannula that automatically and continuously clears the suction tube and at the same time does not appreciably reduce the vacuum available at the distal end of the cannula. In prior art devices such as that described in the Johnson patent, air is vented intermittently, i.e., it is either being vented or not vented. In normal operation, there is no venting. Venting is generally employed only for brief periods of time to clear existing problems in the flow of aspirated material through the cannula. When venting does occur, typical air flow rates are above 2 cfm and as high as 5 cfm (i.e., 120 to 300 cubic feet per hour). It has now been discovered that if venting of air is employed continuously but controlled to small amounts, i.e, between about 3 cubic feet per hour and 40 cubic feet per hour, as measured with the entry ports completely occluded, then an improved overall suction performance is obtained. If the controlled precision leak is less than the 3 cubic feet per hour, no appreciable increase in performance is obtained. The performance of the cannula is greatly reduced if the continuous, controlled air flow is more than 40 cubic feet per hour. In the latter case, the effective vacuum available at the distal end of the cannula is reduced to such a degree that a aspiration of tissue is difficult to obtain.

The continuous precision leak adds ambient air to the suction path optimally where the cannula tube joins the cannula handle so that the average viscosity of the tissue and fluids moving in the suction path is reduced, thereby providing a decreased resistance to flow. Further, the continuous precision leak causes the tissue and fluids to move down the suction tubing in smaller separated segments, thereby eliminating the tendency to have the tissue and fluids bunch into long segments with trapped air between them. Still further, it has been discovered that the precision leak must be continuous to provide an improvement in suction performance. If an on/off approach is used, such as a valve or a thumb vent, then the average viscosity of the tissue and fluids is not reduced on a continual basis and no improvement occurs.

In general the surgical suction device for aspiration of tissues and fluids from a patient is comprised of a proximal connection, a hollow cannula, a blunt distal tip with at least one port for the entry of fragmented tissue into the cannula, and a continuous precision "leak" or vent. The proximal connection is in fluid communication with a source of suction. The source of suction may be the wall suction present in the operating room or it may be from a separate suction pump specifically designed for the lipoplasty procedure. Usually a length of suction tubing is used to connect the suction pump to the proximal connection. The suction tubing is usually a flexible polymer tube. The typical shape of the proximal connection is a hollow tubing barb that connects to the suction tubing. The hollow cannula extends from the proximal connection and has a cannula lumen extending therewithin. The cannula is typically fabricated from stainless steel hypodermic tubing. The cannula lumen is in fluid communication with the source of suction through the proximal connection. The blunt distal tip of the hollow cannula has at least one entry port. The entry port or ports provide a fluid communication path between the cannula lumen and the tissues or fluids of the patient. The entry ports are cut or machined into the sides of the cannula near the blunt distal tip.

The continuous precision leak allows ambient air to pass into the suction path anywhere from the proximal end of the cannula where it joins the handle to the handle connection with the suction tubing so that the average viscosity of the aspirated tissue and fluids is reduced. The continuous precision leak is characterized by providing an air flow of at least 3 cubic feet per hour but not more than 40 cubic feet per hour as measured when the entry port or ports are completely occluded. The continuous precision leak may be formed by placing appropriately sized holes in the cannula or the proximal connection. The proximal end of the cannula, near the proximal connection, is the preferred location for the holes. The surgical suction device with the continuous precision leak may be integrated into a reciprocating mechanism so that the cannula and blunt distal tip move back and forth in a linear fashion.

In a preferred embodiment the surgical suction device may have a hollow handle with the proximal connection on one end and the hollow cannula extending from the other end. The hollow handle is manipulated by the surgeon to direct the hollow cannula and blunt distal tip to the desired location in the patient. The hollow handle has a handle lumen that may be larger in diameter than the cannula lumen and provides a path of fluid communication between the source of suction attached to the proximal connection and the cannula lumen. The hollow handle may be fabricated from any appropriate material such as stainless steel, aluminum, or Delrin®. The preferred method for joining the hollow cannula to the hollow handle is a threaded joint. In this embodiment the threaded joint may form a pathway for the continuous precision leak. The mating faces of the threads provide small pathways for the air to leak into the handle lumen.

A method of using a surgical suction device with a continuous precision leak is also claimed. The method has the steps of inserting a surgical suction device with a continuous precision leak into a medium, applying suction to a proximal connection of the surgical suction device, manipulating the surgical suction device within the medium to the desired areas, sucking or aspirating the medium, and removing the surgical suction device from the medium.

III. BRIEF DESCRIPTION OF THE DRAWINGS

The novel features of the invention are set forth in the appended claims. The invention will be best understood by reference to the following figures when read in conjunction with the detailed description of the invention.

IV. DETAILED DESCRIPTION OF THE INVENTION

Figure 1:
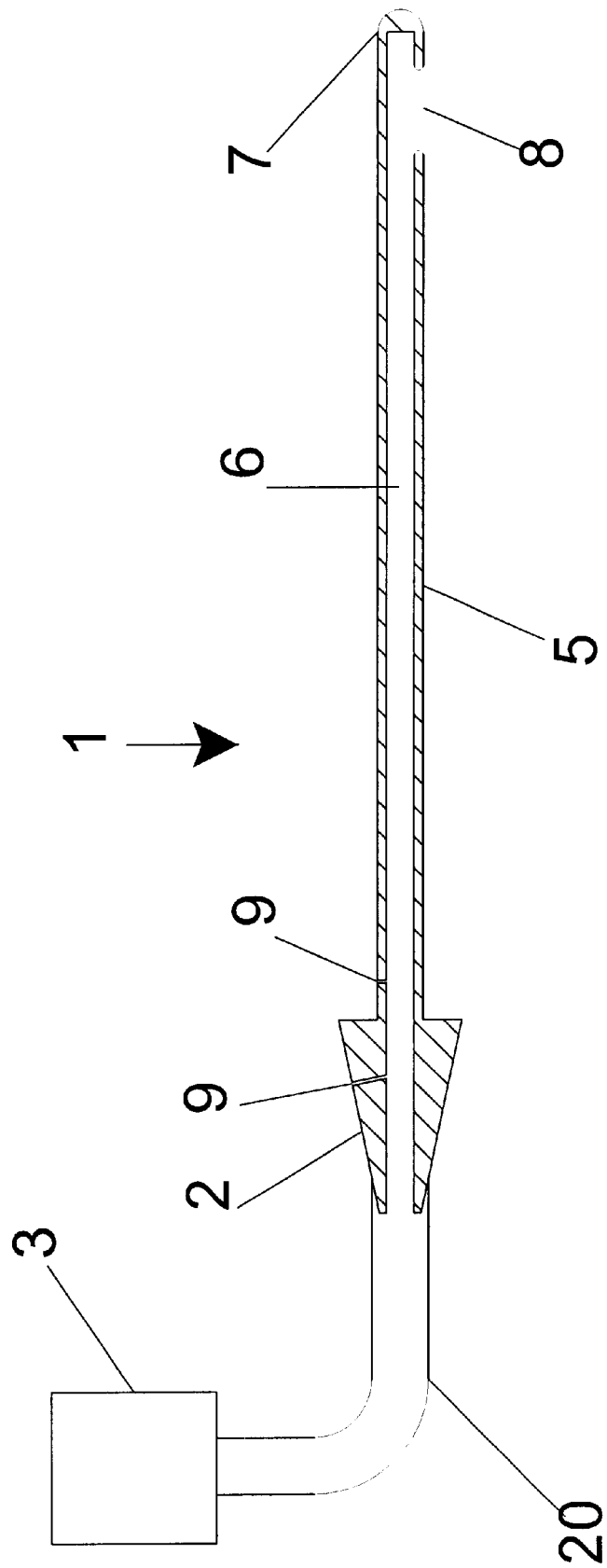
FIG. 1 shows a cross-sectional view of the basic elements of a surgical suction device configured for continuous, precise venting of air.

Referring to the drawings, FIG. 1 shows the basic elements of the surgical suction device 1. The device has a proximal connection 2 that is in fluid communication with a source of suction 3. The source of suction may be the wall suction present in the operating room or it may be from a separate suction pump specifically designed for the lipoplasty procedure. Usually a length of suction tubing 20 will be used to connect the source of suction 3 to the proximal connection 2. The suction tubing is usually flexible polymer tubing. The typical shape of the proximal connection is a hollow tubing barb that connects to the suction tubing. A hollow cannula 5 extends from the proximal connection 2 and has a cannula lumen 6 extending therewithin. The hollow cannula 5 is usually fabricated from stainless steel hypodermic tubing. The cannula lumen 6 is in fluid communication with the source of suction through the proximal connection 2. A blunt distal tip 7 of the hollow cannula 5 has at least one entry port 8. The entry port 8 or ports provide a fluid communication path between the cannula lumen 6 and the tissues or fluids of the patient. The entry ports are cut or machined into the sides of the cannula near the blunt distal tip.

A continuous precision "leak" 9 allows ambient air to pass into the cannula lumen or the proximal connection so that the average viscosity of the aspirated tissue and fluids is reduced. The continuous precision leak 9 is characterized by providing airflow of at least about 3 cubic feet per hour but not more than about 40 cubic feet per hour as measured when the entry port or ports are completely occluded. The preferred range is between 5 cubic feet per hour and 15 cubic feet per hour. While the air flow should be continuous, the rate of air flow may vary within these ranges.

The continuous precision "leak" 9 may be formed by placing appropriately sized holes, e.g., between about 0.005 inches and 0.015 inches in diameter, in either the hollow cannula 5 or the proximal connection 2, as shown in FIG. 1. Alternative means may be employed as demonstrated, for example, by the embodiment depicted in FIG. 2.

The airflow of the continuous precision leak may best be measured using a flow meter such as the model RMB-51 or model RMB-53 manufactured by Dwyer, Michigan City, Ind., USA. The flow meter is placed in series with the suction tubing and the entry ports of the hollow cannula are completely occluded using any reliable technique. For example, the entry ports could be covered with a rubber sleeve of appropriate tightness or they could be filled with a sealant such epoxy. When the entry ports are completely occluded any remaining airflow must come from the continuous precision leak.

Figure 2:
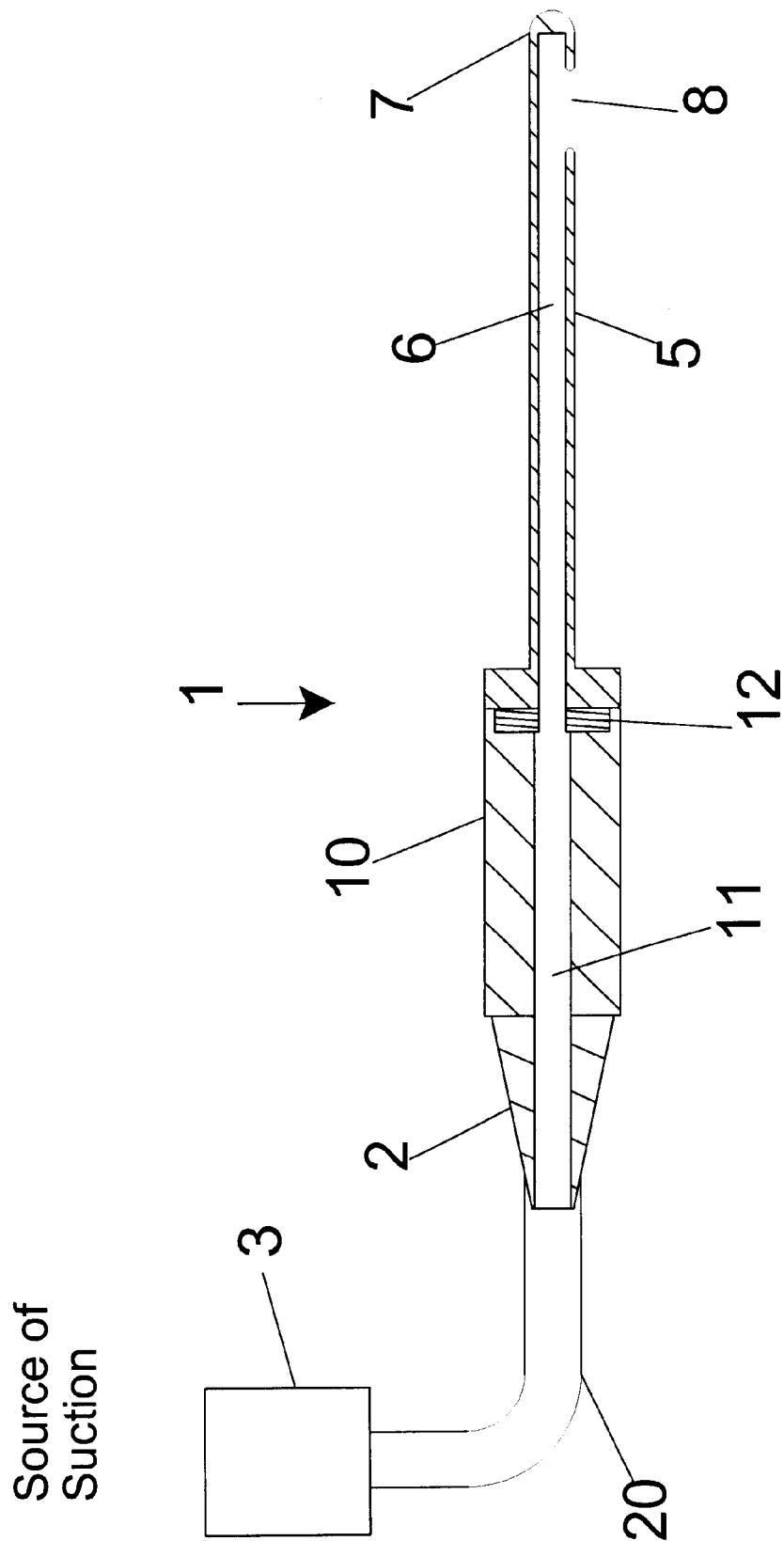
FIG. 2 shows a cross-sectional view of a preferred embodiment of the surgical device that for continuous, precise venting of air through a hollow handle.

FIG. 2 shows a preferred embodiment the surgical suction device 1 which may have a hollow handle 10 with a proximal connection 2 on one end and a hollow cannula 5 extending from the other end. The hollow handle 10 is manipulated by the surgeon to direct the hollow cannula 5 and a blunt distal tip 7 to the desired location in the patient. The hollow handle 10 has a handle lumen 11 that may be larger in diameter than the cannula lumen 6 and provides a path of fluid communication between the source of suction 3 attached to the proximal connection 2 and the cannula lumen 6 through a length of suction tubing 20. The hollow handle 10 may be fabricated from any appropriate material such as stainless steel, aluminum, or Delrin®. The preferred method for joining the hollow cannula 5 to the hollow handle 10 is a threaded joint 12. In this embodiment the threaded joint 12 may form the continuous precision leak. The mating faces of the threads provide small pathways for the air to leak into the handle lumen 11. The amount of continuous precision leak can be adjusted by controlling the 'tightness' or 'looseness' of the threaded joint 12 in the machining process. Small machined contours in the surfaces between the hollow handle 10 and the hollow cannula 5 allow the ambient air to reach the threaded joint.

What is claimed is:

1. A surgical suction device for aspiration of tissues and fluids from a patient comprising:

a proximal connection, the proximal connection in fluid communication with a source of suction;

a hollow cannula extending from the proximal connection, the hollow cannula with a cannula lumen extending therewithin in fluid communication with the source of suction;

a distal tip of the hollow cannula with at least one entry port, the entry port or ports providing a fluid communication path between the cannula lumen and the tissues or fluids of the patient; and a continuous precision leak between the ambient air and the cannula lumen, wherein the continuous precision leak is characterized by providing an air flow of at least 3 cubic feet per hour but not more than 40 cubic feet per hour when the entry port or ports are completely occluded.

2. The surgical suction device of claim 1 wherein the continuous precision leak reduces the maximum no-flow vacuum of the suction source by no more than one inch of mercury when the entry port or ports are completely occluded.

3. The surgical suction device of claim 1 wherein the surgical suction device has a handle for manipulation by a surgeon.

4. The surgical suction device of claim 1 wherein the hollow cannula is a reciprocating device.

5. The surgical suction device of claim 1 wherein the continuous precision leak is formed by appropriately sized holes in the cannula.

6. The surgical suction device of claim 1 wherein the continuous precision leak is formed by appropriately sized holes in the proximal connection.

7. The surgical suction device of claim 1 wherein the continuous precision leak permits the air flow to be varied from time-to-time within the range of at least about 3 cubic feet per hour but not more than about 40 cubic feet per hour when the entry port or ports are completely occluded.

8. A surgical suction device for aspiration of tissues and fluids from a patient comprising:
- a proximal connection, the proximal connection in fluid communication with a source of suction;
- a hollow handle extending from the proximal connection, the hollow handle with a handle lumen extending therewithin in fluid communication with the source of suction;
- a hollow cannula extending from the hollow handle, the hollow cannula with a cannula lumen extending therewithin in fluid communication with the handle lumen and the source of suction;
- a distal tip of the hollow cannula with at least one entry port, the entry port or ports providing a fluid communication path between the cannula lumen and the tissues or fluids of the patient; and
- a continuous precision leak between the ambient air and the handle lumen,
- wherein the continuous precision leak is characterized by providing an air flow of at least about 3 cubic feet per hour but not more than about 40 cubic feet per hour when the entry port or ports are completely occluded.

9. The surgical suction device of claim 8 wherein the handle lumen is a larger diameter than the cannula lumen.

10. The surgical suction device of claim 8 wherein the continuous precision leak is formed by a threaded joint between the hollow cannula and the hollow handle.

11. The surgical suction device of claim 8 wherein the continuous precision leak is formed by a appropriately sized holes in the hollow handle.

12. The surgical suction device of claim 8 wherein the hollow cannula is a reciprocating device.

13. The surgical suction device of claim 8 wherein the continuous precision leak permits the air flow to be varied from time-to-time within the range of at least about 3 cubic feet per hour but not more than about 40 cubic feet per hour when the entry port or ports are completely occluded.

14. A method of using a surgical suction device for the aspiration of a medium, the method having the steps of:
- inserting a suction device with a continuous precision leak into a medium, the continuous precision leak characterized by providing an air flow of at least about 3 cubic feet per hour but not more than about 40 cubic feet per hour when the entry port or ports are completely occluded;
- applying suction to a proximal connection of the surgical suction device;
- using a handle of the surgical suction device to manipulate the distal tip of the device within the medium to the desired areas;
- aspirating the medium, and
- removing the surgical suction device from the medium.

15. The method of claim 14 wherein the continuous precision leak is controlled or varied from time-to-time to provide different air flows within the range of at least about 3 cubic feet per hour but not more than about 40 cubic feet per hour when the entry port or ports are completely occluded.

* * * * *